United States Patent [19]

Halmann et al.

[11] 4,302,534
[45] Nov. 24, 1981

[54] CHEMILUMINESCENT ENZYME IMMUNOASSAY

[75] Inventors: Mirjam Halmann, Rehovot; Baruch Velan, Rishon Lezion; Tamar Seri, Cholon, all of Israel

[73] Assignee: Israel Institute for Biological Research, Ness Ziona, Israel

[21] Appl. No.: 884,104

[22] Filed: Mar. 7, 1978

[30] Foreign Application Priority Data

Mar. 16, 1977 [IL] Israel ............................ 51668

[51] Int. Cl.³ .................... G01N 33/54; C12Q 1/68; C12M 1/34
[52] U.S. Cl. .................................. 435/6; 435/7; 435/8; 435/291; 23/230 B; 424/8; 424/12; 422/52
[58] Field of Search ............ 195/103.5 A, 103.5 L, 195/103.5 R, 127; 23/230 B; 424/2, 8, 12; 435/7, 8, 291, 28, 6, 34; 422/52

[56] References Cited

U.S. PATENT DOCUMENTS 3,359,973 12/1967 Hoffman ...................... 195/103.5 L
3,575,812  4/1971 Chappelle .................... 195/103.5 L
3,791,932  2/1974 Schuurs et al. ........................ 435/7
3,852,157 12/1974 Rubenstein et al. ......... 195/103.5 L
3,999,948 12/1976 Deindoerfer et al. ............. 195/127
4,101,383  7/1978 Wyatt et al. ................. 195/103.5 A
4,104,029  8/1978 Maier .......................... 195/103.5 A
4,134,792  1/1979 Boguslaski et al. ..................... 435/7

FOREIGN PATENT DOCUMENTS 2618419 11/1976 Fed. Rep. of Germany .
2618511 11/1976 Fed. Rep. of Germany .

OTHER PUBLICATIONS

Mahler, et al., *Biological Chemistry*, Harper and Row, New York, (1966), pp. 578-580 and 590-592.
Arakawa, et al., "Enzyme Immunoassay of Cortisol by Chemiluminescence of Luminol-Peroxidase", *Banseki Kagaku*, vol. 26 (1977).
O'Brien, et al., "Generation of Bio-Electronic Energy by Electron Transfer; Reduction of Peroxides Compound I and Compound II by Eosine", *Biochem. Biophys. Res. Comm.*, vol. 81, No. 1, (1978), pp. 75-81.
Halmann, et al., "Peroxidase Mediated Chemiluminescence with Phenol Derivatives. Physicochemical Parameters and Uses in Biological Assays", *Photochem. Photobiol.*, vol. 30 (1979), pp. 165-167.
Velian et al., "Chemiluminescence Immunoassay; A New Sensitive Method for Determination of Antigens" *Immuno-Chemistry*, vol. 15, (1978), pp. 331-333.
Velian et al., "Solid Phase Chemiluminescent Immunoassay" *Proc. Int. Sym. Anal. App. Biolum. and Chemilum.*, (Brussels, 1978), pp. 431-437.

*Primary Examiner*—Thomas G. Wiseman
*Attorney, Agent, or Firm*—Ladas & Parry

[57] ABSTRACT

A heterogeneous enzymatic immunoassay, in which chemiluminescence is employed as a detection means, is disclosed. The chemiluminescence is produced by an enzymatic catalyzed redox reaction between hydrogen peroxide and a phenolic compound such as pyrogallol, resorcinol, phloroglucinol and hydroquinone. The assay is disclosed as having sensitivity equal to that of radioimmunoassays and reverse hemaglutination tests without some of the drawbacks of these methods, e.g., radioactivity hazards.

3 Claims, No Drawings

CHEMILUMINESCENT ENZYME IMMUNOASSAY

BACKGROUND OF THE INVENTION

There exist many methods for the determination of small quantities of biological substances, such as proteins, peptides, polysaccharides, lipids, steroids, hormones, viruses, enzymes, bacteria, and the like.

One type of reaction which has gained importance during recent years is the immunoassay, which has many variations. Any substance with antigenic properties, or which can form an antigen when suitably linked to another substance can be used for such quantitative determinations.

Generally the quantitative measurements in immunoassays are either carried out directly after an immunoreaction, or by measuring a "tag" attached to one of the components of the immunocomplex, i.e. the antigen or the antibody. The tags can be colored or produce color after a reaction; they may be fluorescent or radioactive. Large particles, such as latex or red blood cells which form readily discernible aggregates, can be used as well. The latter are amongst the most sensitive methods known hitherto.

One specific type of immunoassay, which makes use of spectrophotometric measurements is the enzyme-linked immunoassay, performed with enzymes such as peroxidase, alkaline phosphatase, and $\beta$-galactosidase as "tags".

SUMMARY OF THE INVENTION

The present invention relates to a novel method for the quantitative determination of biological substances. The term "biological substances" is intended to include immunogens and antibodies, i.e. substances such as proteins, peptides, glucopeptides, polysaccharides, lipoproteins, lipids, steroids, viruses, bacteria, toxins, etc. In general, the novel method can be applied for the quantitative determination of any compound or entity which elicits antibody formation when injected into an animal, or which can be bound to another substance, and the thus obtained conjugate will elicit antibody formation when injected into an animal. The novel method is based on the use of an enzymatic tag, on the enzymatic oxidation of a phenolic compound such as pyrogallol, resorcinol, phloroglucinol, hydroxyhydroquinone, active derivatives of these, or cyclic or other chemiluminescent compounds which are substrates for peroxides which emit light when oxidized, and on the measurement of photons emitted during said enzymatic oxidation. The novel method makes possible the quantitative determination of very small amounts of substances and entities as defined above, and the sensitivity is better than that of enzyme linked immunoreactions with peroxidase using color forming reactions, and spectrophotometric measurements and which can be performed in the same order of magnitude of time. The sensitivity of the novel assay is about equal to that of radioimmunoassays and that of reverse hemaglutination tests, but does not have some of the drawbacks of these methods. For example, it may be performed by any personnel in all laboratories without the need of extra precaution as when $I^{125}$ is used.

The present invention also relates to kits, to specific light measurement apparatus, and other appliances and components adapted to be used in the novel assay.

Other and further aspects of the invention will become apparent from the following detailed description.

The process for the quantitative determination of biological materials, as defined before, according to the present invention comprises the following steps:
 a. Tagging;
 b. Immunoreaction;
 c. Enzymatic reaction;
 d. Measurement of light-emission.

The tage used is a suitable peroxidase. Amongst suitable peroxidases there may be mentioned horseradish peroxidase, lactoperoxidase, turnip peroxidase, etc.

Horseradish peroxidase is widely used in cytology and cytochemistry for microscopy and electron-microscopy staining. The enzyme can be linked to antibodies against the substance to be determined. After immunoreaction between this conjugate and the substance, the latter can be detected by a precipitate which is formed around the enzyme antigen-antibody complex, when the enzyme catalyzes the oxidation of diaminobenzidine by hydrogen peroxide. There exist also other peroxidase-linked immunoassays but in all of these the enzyme is determined by the spectrophotometric measurement of the color produced during or after the reaction with a suitable reducing agent and with hydrogen peroxide.

Tagging of Antibodies with Peroxidase:

Various techniques are known. Nakane et al, J. Histo. Chem. Cytochem. 14, 929 (1966) developed the conjugation with 4,4'-difluoro-3,3'-dinitrodiphenyl sulfone. Avrameas, Immunochem. 6, 43 (1969) developed conjugation with glutaraldehyde, and Avrameas et al, Immunochem. 8, 1175 (1971) developed a two stage conjugation with glutaraldehye. Nakane et al., J. Histochem. Cytochem., 22, 1084 (1974) developed a method of linking peroxidase through its sugar moiety to globulin. Sternberger et al., J. Histochem. Cytochem. 18, 315 (1970) developed an unlabelled antibody method.

The antibody homologous to the antigen tested can also be used in its original form and peroxidase can be linked to an antibody against globulin of the animal in which the first antibody was prepared. Two successive immunoreactions are carried out. Peroxidase can be linked to staphylococcal protein A which has a high affinity to the Fc region of $\gamma$-globulins. In this case too, two immunoreactions must be carried out.

Tagging of Antigens with Peroxidase:

The conjugation method used depends on the functional groups available. When amino groups can be used, the method based on the use of difluoro-dinitrophenyl sulfone can be resorted to. In this case also methods based on glutaraldehyde can be used. When a sugar moiety is available, the method of Nakane et al. can be used. It is clear that the binding ought to be via such groups, that the antigenic and enzymatic properties of the conjugate will not be substantially impaired.

The following illustrates some of the principles of the assay:

The Immunoreaction:

a. Direct Determination of the Substance with Homologous Antibody Conjugated to Peroxidase.

A variety of procedures can be resorted to, based on the immunoreaction and on the separation of conjugate in excess. When the immunoreaction is followed by a precipitation of the complex, the precipitate can be determined. When no precipitation takes place, the homologous antibody can be tagged and a second antibody against globulin of the animal used as the first antibody will precipitate the entire complex (double antibody method). The thus obtained precipitate is washed and centrifuged as in the first case.

It is possible to fix the antibody to a film with low nonspecific adsorption, such as Aclar (T.M.) or Mylar (T.M.). Fixation can be effected with acetone, methanol, heating, etc., the condition being not to substantially decrease the antigenic properties. Tagged antibody is added and after incubation and washing the film is tested for peroxidase content. The double antibody method, peroxidase antiperoxidase soluble complex, or protein A peroxidase conjugate method can be used.

b. Competition assays corresponding to radioimmunoassays can be performed with homologous antibody covalently attached to Sepharose, Sephadex, cellulose, enzacryl, carboxy methyl cellulose or the like. The antigen-peroxidase conjugate competes with the unknown antigen solution for the fixed antibody.

c. Solid phase immunoassays can be performed in two ways—first, by adsorption of a specific antibody to a solid support (polystyrene, polyvinylchloride etc), immunoreaction of the antigen to the fixed antibody, and determination of the antigen by peroxidase tagged antibody;

second, using competitive assays where either tagged antigen competes with the unknown antigen for the fixed antibody or where the second antibody—which is tagged—measures the competition between antigen bound to the solid phase and the unknown antigen, which is in solution.

d. In another form, the antigen can be bound to the solid support and the reaction effected in the inverse form.

All the above types of reactions can be carried out in an inverse manner for the determination of antibody.

The time required for the immunoreactions varies, levelling off takes generally between 1 minute to 2 hours. Other conditions, such as temperature, preadsorption with normal serum, wash solutions, etc., are as conventionally used in immunoreactions.

The Enzymatic Reaction:

Chemiluminescence during oxidation of pyrogallol was described by Lenard et al, Ann. Phys. und Chemie, 34 (1888) 918. Catalysis of this reaction by horseradish peroxidase was described by Ahnstrom et al, Acta Chem. Scan. 15 (1961) 1417. Nilsson in Acta Chem. Scan. 18 (1964) 389, Ahnström in Acta. Chem. Scan. 19 (1965) 300 and Ahnström et al., Acta. Chem. Scan. 19 (1965) 313. The last of these reports states that also resorcinol gives a detectable luminescence.

According to the present invention, an improved method is provided for the quantitative determination of small quantities of peroxidase (of the order of as low as $10^{-15}$ moles) which compares favorably with known methods. Studies carried out Halmann et al., App. Environ. Microbiol. 34 (1977) 473, Velan et al., Immunochem. (1978) in press, have provided data on the suitable conditions for light emission and its measurement. Various phenol-type compounds can be used as reducing agents, and amongst others pyrogallol, resorcinol, phloroglucinol, and hydroxyhydroquinone were found to be suitable.

Amongst suitable peroxidases are horseradish peroxidase, turnip peroxidase, sweet potato peroxidase, other vegetable peroxidases, lactoperoxidase, etc.

Amongst oxidants suitable for the reaction according to the present invention, there may be mentioned in addition to hydrogen peroxide permethanol, perethanol and urea hydrogen peroxide.

The sample to be determined is introduced into a small reaction tube after immunoreaction and after discarding excess of reagent. Typically 50 μl of a 0.2% solution of pyrogallol in 0.18 M phosphate buffer, pH 6.5, are added and the reaction is started by addition of 50 μl of 0.25% hydrogen peroxide.

Measurement of Light Emission:

The maximum of light emission occurs generally between 3 to 90 seconds after initiation of the reaction. The period of time depends on the quantity and nature of the enzyme present.

Basically there can be used any system of adequate sensitivity which measures either the maximum of light intensity during the chemiluminescent reaction or the total quantity of light emitted during such reaction.

Devices to be used in measuring the light emitted during the reaction according to the present invention comprise means for holding in place a suitable reaction vessel, means for amplifying the light emitted, and a readout or recording system.

By a modification of the above, the amount of light emitted is integrated. According to yet a further modification, means are provided for measuring the rate of change of light intensity during the reaction, and determining the maximum of the rate of change.

The maximum of light emission intensity can also be measured and used as a determining value. The results can be read from calibration curves, see for instance, Velan et al., Immunochem., (1978), in press.

The most suitable method of measurement of the chemiluminescence is determined and this makes possible very sensitive assays or high accuracy.

The method may be carried out in practically continuous manner. For such continuous testing procedure there is provided a supply of tape, made of resilient inert material, such as a plastic tape which is moved by means of a suitable mechanical device in a continuous manner or in a stepwise fashion according to a predetermined program. The tape moves first through a sampler wherein the sample to be tested is applied to a discrete spot of the tape, fixation may be effected by means of heat, methanol or other conventional means; the tape is moved to the next step, namely through a preadsorption solution such as normal serum and tris-buffer; to the next step where it is passed through the immunoreaction solution (antibody-linked peroxidase), to the next step which is a wash-solution such as saline and from there into the apparatus for the chemiluminescent determination of the peroxidase where the reaction mixture is applied to the sample and the light emission is measured. The sequence of movement or its speed is such that individual samples are measured in the apparatus. This is best effected by recording light emission up to a maximum of about 90 seconds or by determining the maximum increment of light emission. Numerical values are obtained by comparison with a calibration curve.

The apparatus for the measurement of the chemiluminescence essentially comprises a light-tight enclosure wherein the reaction vessel is located, a mirror being provided for concentrating a maximum of the emitted light onto a photomultiplier located in the same housing, said photomultiplier being connected in a conventional manner via an amplifier to recording or readout means. According to a preferred embodiment either maximum luminescence up to about 90" is measured or the maximum increment of light emission during the chemiluminescence reaction of the peroxidase is measured. The reaction vessel is advantageously a small cuvette containing the sample, means being provided for adding a predetermined quantity of the reaction mixture so as to commence the chemiluminescence reaction.

The assay is generally carried out by comparison of a standard sample with the sample which is examined, and thus the method of measurement gives values which are reliable and correspond to the correct quantity of the entity which is determined.

Sensitivity of the Method:

It was possible to detect and determine $10^2$ to $10^3$ microorganisms which is about 10 times less than determinable by the immunoradiometric assay based on the use of $I^{125}$. With the same antibody labelled with 1 or 2 atoms $I^{125}$ per molecule only $10^4$ bacteria could be detected. Using a competition assay with antibody linked to Sepharose 1 nanogram enterotoxin B was detected, which is also the lower limit of sensitivity of a radioimmunoassay with protein labelled with 3 $I^{125}$ atoms per molecule. Reversed hemaglutination with the same reagents gave similar results. Peroxidase can be determined directly on a scale of $10^3$ to $10^4$ without necessity to resort to dilutions.

The shelf life of peroxidase conjugates and of peroxidase-antiperoxidase soluble complex is of the order of years. This is a considerable improvement over the shelf life of about one month of $I^{125}$ iodinated reagents used in radio-immunoassays.

The invention is demonstrated with reference to the following examples, which are of an illustrative nature only and which are to be construed in a non-limitative sense.

EXAMPLE 1: Determination—Serratia marcescens

Serratia marcescens was grown overnight at room temperature on slants of 2% Tryptose (Difco), 0.5% NaCl solidified with 1.5% Bacto agar. The products were suspended in saline and diluted to an optical density of 0.200 which corresponds to about $10^8$ cells/ml.

Anti-Serratia serum was prepared by immunizing rats weekly by i.v. injections of 1 ml of increasing concentrations of S. marcescens ($5 \times 10^6$ to $10^8$ cells). After seven weeks the animals were bled and the serum was separated.

Anti-Serratia γ-globulin was prepared by dialyzing 10 ml of anti-serratia serum against three 1 liter changes of phosphate buffer, pH 8.0, 0.03 M and by chromatography on a column of DEAE cellulose $2.5 \times 15$ cm equilibrated with the same buffer. The first fraction of the protein which was not absorbed by the column was collected.

Anti-Serratia peroxidase conjugate was prepared according to the two-step method of Avrameas: Immunochem, 8 1175 (1971), but the conjugate was not separated from the peroxidase in excess. The free peroxidase does not increase the blank of the bacterial determination.

10 mg of peroxidase (Sigma RZ 3.0) were dissolved in 0.2 ml of 0.1 M phosphate buffer of pH 6.8 containing 1.25% glutaraldehyde (Sigma). After 24 hours at 4° the reaction mixture was passed through a Sephadex G-25 column $0.8 \times 15$ cm equilibrated with saline and the fraction containing the enzyme was collected. Anti-serratia γ-globulin solution containing 5 mg protein and 0.1 ml of 1 M carbonate buffer pH 9.5 were added to the enzyme. After 24 hours at 4° C. 0.1 ml of 0.2 M lysine was added and after 2 hours it was dialyzed against $4 \times 1$ liter saline. The thus obtained conjugate was stored at 4° C.

Test for Serratia

Serial dilution of bacteria in saline containing $3 \times 10^7$, $10^7$, $3 \times 10^6$, $10^6$, and $3 \times 10^5$ cells per milliliter were prepared and 1 μl aliquots of saline and of increasing concentrations of the bacterial suspensions were put on an Aclar 33 (Allied Chemical Co) strip of $3.5 \times 45$ mm, 6 drops on each strip. The strips were positioned in a plastic petri dish and dried by a temperature grandient of hot water under the dish and dry ice on the cover. 5 μl drops of methanol were added to each bacterial spot which can be perceived due to the sodium chloride present and the strips were left to dry. The strips with the fixed bacteria were placed in small test tubes, washed with 0.05 M tris HCl, pH 7.6 in saline. To avoid non-specific adsorption 0.8 ml of Tris-saline supernatant of Salmonella suspension and normal goat serum in a proportion of 10/4/2 were added. After 10 minutes incubation 50 μl of anti-Serratia peroxidase conjugate were added to the precipitation solution, mixed gently and left for 10 minutes at room temperature and 5 minutes at 0° C. The strips were then washed 3 times with Tris-saline.

The strips were cut according to the bacterial spots which were previously marked on millimeter-paper and each piece was introduced separately into a $9 \times 50$ mm reaction cuvette. To each cuvette 50 μl of 0.2% pyrogallol (Merck Co) in 0.18 M phosphate buffer, pH 6.5 were added. The cuvette was introduced into the light-measuring apparatus and 50 μl of 0.25% hydrogen peroxide (Perhydrol, Merck) in 0.18 M phosphate buffer of pH 6.5 were added. Light emission was measured.

Table 1 shows the data obtained when 50 μl conjugate were used. The light measuring apparatus was a Dupont Luminiscence Biometer, set at coarse sensitivity at 8 and exponent dial with minimum value at 3. Light intensity measurements were carried out at 3 second intervals up to maximal value.

TABLE I

| Determination of S. marcescens with anti-serratia-peroxidase conjugate | |
|---|---|
| No. of bacteria | Readings (duplicate) |
| 0 | $2.3 \times 10^2$–$2.9 \times 10^2$ |
| 300 | $6.8 \times 10^2$–$5.3 \times 10^2$ |
| 1000 | $1.6 \times 10^3$–$2.5 \times 10^3$ |
| 3000 | $3.6 \times 10^3$–$7.4 \times 10^3$ |
| 10.000 | $1.1 \times 10^4$–$1.6 \times 10^4$ |
| 30.000 | $3.5 \times 10^4$–$4.1 \times 10^4$ |

EXAMPLE 2: Determination of Staphylococcal Enterotoxin B (SEB)

This determination was based on the competition of the unknown sample with a known quantity of SEB linked to peroxidase for the homologous antibody attached to Sepharose.

Preparation of Antibody against SEB:

SEB was purified by the method of Schantz et al, Biochemistry: 4, 1011 (1965). Rabbits were immunized by five subcutaneous injections of 1,2,5,10 and 20 mg, of SEB with adjuvant at intervals of ten days. The animals were bled two weeks after the last injection. The serum obtained contained 8 mg anti-SEB globulin/ml. The globulin fraction of the serum was precipitated with 17% sodium sulfate at room temperature and dissolved in PBS to give a concentration of 20 mg protein/milliliter.

Binding of Globulin to Sepharose:

5 mg of globulin were attached to 0.5 g (dry weight) of CN Br-activated Sepharose 4B (Pharmacia), and the yield was over 90%. The process was effected in 0.1 N sodium bicarbonate at room temperature during 18 hours. The gel particles were washed and remaining active groups on the Sepharose were neutralized with 1 M ethanolamine, pH 8. Protein which was not bound to the Sepharose was removed by repeated washings with 0.5 M acetate buffer, pH 4 and 0.5 M sodium bicarbonate, pH 8. Sepharose beads with lower concentration of anti-SEB were prepared with a mixture of Anti-SEB and globulin of normal rabbits in variable proportions.

Linkage of Peroxidase with SEB:

This was performed according to Avrameas, see Example 1, and the conjugate obtained was separated from free peroxidase and free SEB by isoelectric focusing at a pH range of pH 6 to 9. The conjugate has three peaks with pH 7.0, 7.4 and 7.8 respectively. The substance of peak pH 7.0 was found to be the most suitable for use as reagent.

Standard Assay Procedure:

0.2 ml of the solution to be tested, 0.1 ml 0.06 M phosphate pH 7.2 in saline containing 2 mg/ml BSA, 5 μg SEB peroxidase conjugate, 0.05 ml of a suspension of anti-SEB-Sepharose (about 1 mg dry weight) were introduced into test tubes of 5×50 mm.

The test tubes were placed on a slightly slanted support and agitated reciprocally parallel to the length of the cuvette. The cuvette rolled forwards and backwards a distance of 1.5 cm about 100 times per minute. After incubation during 2 hours the Sepharose was separated by 1 minute centrifugation at 800 g, the supernatant was discarded and the sediment was washed twice with 0.18 M phosphate buffer pH 6.5. Peroxidase bound to the Sepharose was determined according to the light emitted when 0.05 ml of 2% pyrogallol and 0.05 ml 0.25% hydrogen peroxide in 0.18 M phosphate buffer pH 6.5 were added.

According to this method it is possible to determine quantitatively from about 0.001 μg to 20 μg SEB depending on the concentration of the anti-SEB on the Sepharose and on the quantity of SEB-peroxidase conjugate used. The following Table indicates the ranges of SEB which were determined.

TABLE 2

| DETERMINATION OF SEB | | | |
|---|---|---|---|
| ANTI-SEB | | SEB PEROXIDASE | RANGE OF |
| Anti-SEB/g | Sepharose Anti-SEB/Assay | Conjugate | SEB Determination |
| 10 mg | 10 μg | 0.5 μg | 0.2 to 20 μg |
| 0.5 mg | 0.5 μg | 0.05 μg | 0.02 to 0.2 μg |
| 0.05 mg | 0.05 μg | 0.005 μg | 0.001 to 0.02 μg |

The results can be read from calibration curves, see for instance Velan et al, Immunochem, 1978 (in press).

EXAMPLE 3: Determination of Staphylococcal Enterotoxin B (SEB) by Solid Phase Immunoassay This determination is based on the non-specific adsorption of antibody on polyvinyl chloride microtitration plates. This antibody is able to attach the homologous antigen from a solution, and the attached antigen can be determined by a solution of the same antibody conjugated to peroxidase.

SEB and anti-SEB antibody were the same as described in Example 2. Anti-SEB-peroxidase-conjugate was prepared in the same manner as anti-Serratia peroxidase conjugate described in Example 1.

Adsorption of Antibody on PVC Microplates:

Aliquots of 50 μl of a 50 μg/ml solution of anti-SEB γ-globulin are pipetted into the wells of the standard microtitration plate (Cooke). After 1 hour at 4° C. the solution is withdrawn and the plate is washed with tris-saline and aliquots of 100 μl of solution of 1 mg/ml BSA are added to the wells. Plates prepared in this manner can be stored for a number of days.

Reaction of SEB with Anti-SEB on PVC:

The BSA solution is withdrawn, the wells are washed with 0.05 M tris-Cl at pH 7 in saline (tris-saline) and 50 μl aliquots of buffer or solutions with increasing concentration of SEB are added to the wells. After 2 hours at room temperature the wells are washed with tris-saline.

Reaction with Anti-SEB Peroxidase Conjugate:

Aliquots of 50 μl of a solution containing 20 μl/ml conjugate are added to the wells. After 2 hours at room temperature the wells are washed with tris-saline.

Chemiluminescent Determination of Peroxidase:

The bottoms of the wells are cut out and introduced into cuvettes. Light emission is determined as described in Example 1 with pyrogallol and hydrogen peroxide. The results are presented in the following Table:

TABLE 3

| SEB (μg/ml) | SEB nano-g in test | Readings (Duplicates) |
|---|---|---|
| 0 | 0 | $0.19 \times 10^3$–$0.31 \times 10^3$ |
| 30 | 1.5 | $2.6 \times 10^3$–$1.58 \times 10^3$ |
| 100 | 5 | $1.58 \times 10^4$–$8.87 \times 10^3$ |
| 300 | 15 | $3.79 \times 10^4$–$4.39 \times 10^4$ |
| 1000 | 50 | $5.97 \times 10^4$–$3.05 \times 10^4$ |
| 3000 | 150 | $6.46 \times 10^4$–$5.9 \times 10^4$ |

We claim:

1. An assay for the quantitative determination of entities selected from the group consisting of immunogens and antibodies, which comprises:

a. contacting and reacting immunologically a sample of the immunogen or of the antibody to be determined with, respectively, an anti immunogen-peroxidase conjugate or with an antigen-peroxidase conjugate specific to said entity, b. removing excess of antigen peroxidase conjugate or immunogen peroxidase conjugate, c. adding a phenolic compound selected from the group consisting of pyrogallol, resorcinol, phloroglucinol and hydroxyhydroquinone and hydrogen peroxide, and d. measuring the light emitted and thus establishing the quantity of the entity to be determined.

2. An assay according to claim 1 wherein the entity determined is selected from enzymes, steroids, proteins, vitamins, hormones, bacteria, viruses and toxins.

3. An assay according to claim 1 wherein the peroxidase is selected from horseradish peroxidase, turnip peroxidase, sweet potato peroxidase or lactoperoxidase.

* * * * *